(12) United States Patent
Yang et al.

(10) Patent No.: US 6,596,013 B2
(45) Date of Patent: Jul. 22, 2003

(54) METHOD AND APPARATUS FOR TREATING SEPTAL DEFECTS

(75) Inventors: Dachuan Yang, Hillsborough, NJ (US); Jaydeep Y. Kokate, Maple Grove, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 125 days.

(21) Appl. No.: 09/957,975

(22) Filed: Sep. 20, 2001

(65) Prior Publication Data

US 2003/0055455 A1 Mar. 20, 2003

(51) Int. Cl.$^7$ ............................................. A61B 17/08
(52) U.S. Cl. ...................... 606/215; 606/213; 606/139
(58) Field of Search .................. 606/213, 215, 606/139, 151; 604/60

(56) References Cited

U.S. PATENT DOCUMENTS

| | | | |
|---|---|---|---|
| 3,874,388 A | 4/1975 | King et al. | |
| 4,007,743 A | 2/1977 | Blake | |
| 4,836,204 A | 6/1989 | Landymore et al. | |
| 4,917,089 A | 4/1990 | Sideris | |
| 5,108,420 A | 4/1992 | Marks | |
| 5,171,259 A | 12/1992 | Inoue | |
| 5,192,301 A | 3/1993 | Kamiya et al. | |
| 5,284,488 A | 2/1994 | Sideris | |
| 5,312,341 A | 5/1994 | Turi | |
| 5,334,217 A | 8/1994 | Das | |
| 5,425,744 A | 6/1995 | Fagan et al. | |
| 5,433,727 A | 7/1995 | Sideris | |
| 5,451,235 A | 9/1995 | Lock et al. | |
| 5,507,811 A | 4/1996 | Koike et al. | |
| 5,578,045 A | 11/1996 | Das | |
| 5,591,206 A | * 1/1997 | Moufarrege | ............... 606/215 |
| 5,634,936 A | 6/1997 | Linden et al. | |
| 5,683,411 A | 11/1997 | Kavteladze et al. | |

(List continued on next page.)

FOREIGN PATENT DOCUMENTS

| | | |
|---|---|---|
| EP | 0 541 063 A2 | 5/1993 |
| EP | 0 545 091 A2 | 6/1993 |
| EP | 0 556 564 A2 | 8/1993 |
| EP | 0 655 222 A1 | 5/1995 |
| GB | 1 509 023 | 4/1975 |
| JP | 8-196623 A | 8/1996 |
| WO | WO 93/13712 A1 | 7/1993 |
| WO | WO 97/28744 A1 | 8/1997 |
| WO | WO 97/41778 A1 | 11/1997 |
| WO | WO 97/41779 A1 | 11/1997 |
| WO | WO 97/42878 A1 | 11/1997 |
| WO | WO 98/27868 A1 | 7/1998 |
| WO | WO 99/39646 A1 | 8/1999 |
| WO | WO 99/40849 A1 | 8/1999 |
| WO | WO 99/41778 A1 | 8/1999 |
| WO | WO 00/10452 A1 | 3/2000 |
| WO | WO 00/12012 A1 | 3/2000 |

OTHER PUBLICATIONS

King, Terry D. et al., "Secundum Atrial Septal Defect," *The Journal of the American Medical Association*, vol. 235, No. 14, Apr. 5, 1976, pp. 2506–2509.

*Primary Examiner*—David O. Reip
*Assistant Examiner*—Gwen Phanijphand
(74) *Attorney, Agent, or Firm*—Crompton, Seager & Tufte, LLC

(57) ABSTRACT

Systems and methods for treating septal defects. A system for treating septal defects may comprise a first catheter having a distal end and a first lumen, a second catheter having a distal end a second lumen, a bridge member extending between the distal end of the first catheter and the distal end of the second catheter, and a first patch adapted to be disposed within the first lumen and movable out of the first lumen along the bridge member. A second patch may be used and be connectable to the first patch.

28 Claims, 2 Drawing Sheets

U.S. PATENT DOCUMENTS

| | | |
|---|---|---|
| 5,702,421 A | 12/1997 | Schneidt |
| 5,709,707 A | 1/1998 | Lock et al. |
| 5,733,294 A | 3/1998 | Forber et al. |
| 5,741,297 A | 4/1998 | Simon |
| 5,797,960 A | 8/1998 | Stevens et al. |
| 5,823,956 A | 10/1998 | Roth et al. |
| 5,829,447 A | 11/1998 | Stevens et al. |
| 5,846,261 A | 12/1998 | Kotula et al. |
| 5,853,422 A | 12/1998 | Huebsch et al. |
| 5,855,614 A | 1/1999 | Stevens et al. |
| 5,860,948 A | 1/1999 | Buscemi |
| 5,861,003 A | 1/1999 | Latson et al. |
| 5,879,366 A | 3/1999 | Shaw et al. |
| 5,904,703 A | 5/1999 | Gilson |
| 5,924,424 A | 7/1999 | Stevens et al. |
| 5,928,250 A | 7/1999 | Koike et al. |
| 5,944,738 A | 8/1999 | Amplatz et al. |
| 5,976,174 A | 11/1999 | Ruiz |
| 6,024,756 A | 2/2000 | Huebsch et al. |
| 6,077,281 A | 6/2000 | Das |
| 6,077,291 A | 6/2000 | Das |
| 6,079,414 A | 6/2000 | Roth |
| 6,080,182 A | 6/2000 | Shaw et al. |
| 6,106,532 A | 8/2000 | Koike, deceased et al. |
| 6,117,159 A | 9/2000 | Huebsch et al. |
| 6,171,329 B1 | 1/2001 | Shaw et al. |
| 6,214,029 B1 | 4/2001 | Thill et al. |

* cited by examiner

METHOD AND APPARATUS FOR TREATING SEPTAL DEFECTS

FIELD OF THE INVENTION

The present invention generally relates to devices and methods for treating septal defects or shunts in the vascular system. More particularly, the present invention relates to devices and methods for treating septal defects within the heart of a human being.

BACKGROUND OF THE INVENTION

Heart defects including abnormal openings within the heart and vascular system may occur either congenitally or by acquisition. These abnormal openings commonly occur across a septum. A septum is generally defined as a thin wall of tissue that divides two or more areas within the body, for example heart chambers.

The most common congenital heart defects include ventricular septal defects, atrial septal defects, and patent ductus arteriosus. Left-to-right ventricular septal defects and patent ductus arteriosus typical result in the left side of the heart having to work harder because some of the blood it pumps will recirculate through the lungs instead of circulating throughout the body. Atrial septal defects typically result in blood being shunted from the left atrium to the right, thus overloading the right side of the heart. These conditions have significant consequences if left untreated including hypertension, increased pulmonary arterial pressure, strain on the heart muscle, and ultimately heart failure.

For many years, septal defects were corrected by open-heart surgery where a surgeon would cut into the heart and suture the defect closed. If the defect was too large to be sutured, a patch of a biologically compatible material could be sewn onto the septum to cover the defect. A variety of methods for treating septal defects that utilize intravascular catheters have been developed as less invasive alternatives to open heart surgery. In general, these methods comprise some form of a patch that is delivered to the defect through an intravascular catheter. The patch is then secured to the defect in order to suitably repair the defect.

One of the first such devices was disclosed by King et al. in U.S. Pat. No. 3,874,388. The King device comprises a pair of mechanical umbrella-like patches that are be connected to one another. Since the disclosure of the King device, a number of septal closure devices have been disclosed and patented. These devices generally have in common the use of a single intravascular catheter that is used to secure a patch to a septal defect. The use of a single catheter can limit the utility of such devices since it may often be difficult to center and place the patch across a small hole within a constantly moving heart. A need, therefore, exists for devices and methods for treating septal defects that have an improved ability to center and place a patch across a septal defect.

SUMMARY OF THE INVENTION

The present invention comprises unique devices and methods for treating septal defects. Moreover, the present invention includes devices and methods for treating septal defects that comprise an improved ability to center and place a patch across a septal defect. The patch system may comprise a first catheter, a second catheter, and a bridge member that may be adapted to extend between the first catheter and the second catheter.

The first catheter and the second catheter may be steered to opposite sides of a septal defect. Once located on opposite sides of a septal defect, the bridge member may be extended so as to pass from a first lumen of the first catheter, through the septal defect, and into a second lumen of the second catheter.

A first patch may be urged toward the septal defect along the bridge member by a first pusher. Similarly, a second pusher may be used to move a second patch over the bridge member toward the septal defect. The first patch and the second patch may be connectable across the septal defect.

In alternative embodiments of the invention, the first patch and the second patch may be connected by differing mechanisms. For example, the first patch may comprise an outer surface having a plurality of loops, and the second patch may comprise an outer surface having a plurality of complementary hooks. The hooks may engage the loops when the first patch and the second patch are brought into contact with one another and substantially remain connected. Alternatively, the first patch and second patch may comprise an outer surface including a magnet or adhesive.

In an exemplary embodiment, the first patch and the second patch may be mechanically connectable. For example, the first patch may comprise an outer surface including a chamber and a deflectable flange. In addition, the second patch may comprise an outer surface including a shank and one or more rings defining a recess therebetween. Preferably, the chamber is adapted to receive the shank and lock in place when the deflectable flange becomes disposed within the recess. Alternatively, the first patch may comprise an outer surface including a chamber having threads, and the second patch may comprise an outer surface including a shank having threads. The second patch may further comprise a head having a slot. An alternative pusher may be used that includes a complementary head adapted to engage the slot. The chamber may be adapted to threadably receive the shank while the complementary head is engaged with the slot.

DETAILED DESCRIPTION OF THE PREFERRED EMBODIMENTS

Figure 1:
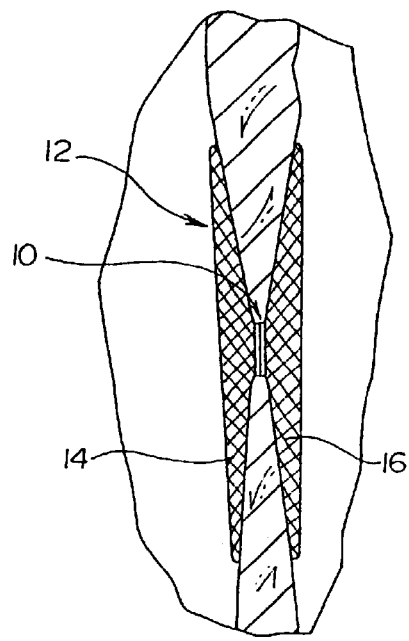
FIG. 1 is a plan view of a patched septal defect, according to a preferred embodiment of the invention.

The following detailed description should be read with reference to the drawings wherein like reference numerals indicate like elements throughout the several views. The detailed description and drawings represent select embodiments and are not intended to be limiting.

FIG. 1 is a plan view of a treated septal defect, according to a preferred embodiment of the invention. A septal defect 10 may be treated by a patch device 12. Patch 12 comprises a first patch 14 and a second patch 16 that are connected across septal defect 10. Septal defect 10 may be located at a number of places within the body of a living being including the heart, between heart chambers including ventricles and atria, blood vessels, and other organs. According to a preferred embodiment, patch device 12 may be used to treat defects including ventricular septal defects, atrial septal defects, and patent ductus arteriosus.

FIGS. 2–6 depict an example of a preferred apparatus and the steps of a preferred method for treating septal defect 110. According to this example, septal defect 110 comprises a hole between the right ventricle 18 and the left ventricle 20 of a human heart.

Figure 2:
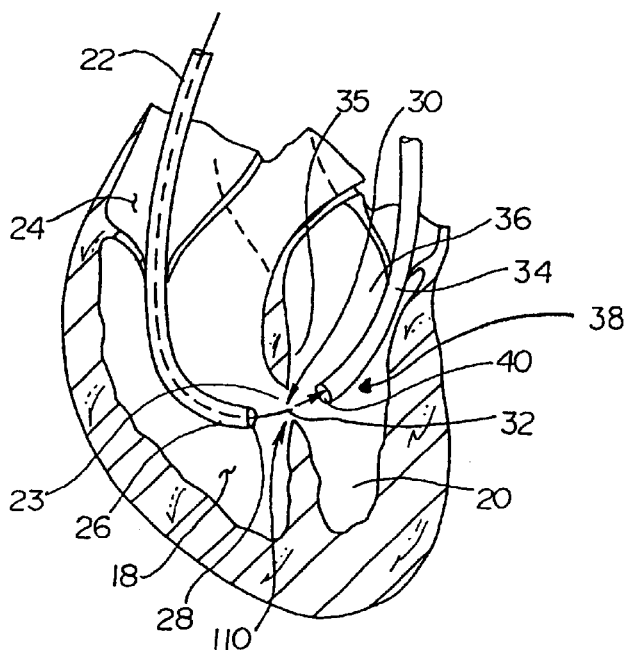
FIG. 2 is a plan view of two catheters approaching a septal defect, according to a preferred embodiment of the invention.

FIG. 2 is a plan view of two catheters approaching septal defect 110. In a preferred embodiment, a first catheter 22 may approach a first side 23 of septal defect 110 by passing through the venous system, into the right atrium 24, and to a location within right ventricle 18 adjacent septal defect 110. Preferably, first catheter 22 comprises a proximal end located outside the patient (not shown), a distal end 26, and a first lumen 28 extending therethrough.

First catheter 22 may be maneuvered through the vasculature of a patient and may comprise a number of different catheter types. For example, first catheter 22 may comprise a guide catheter that is adapted to pass over a guidewire. According to a preferred embodiment, first catheter 22 comprises materials that include a level of steerability, flexibility, and torquability suitable for passing through the vasculature of a patient.

Because congenital heart defects may be diagnosed in children, the present invention includes an embodiment wherein first catheter 22 may be sized appropriately for use in pediatric patients. For pediatric patients, the outside diameter of first catheter 22 may be less than about 5 cm. More preferably, the outside diameter may be less than about 2 cm. First catheter 22 may also be used for adult patients, wherein the outside diameter of first catheter 22 may be less than about 5 cm. More preferably, the outside diameter may be about less than about 2 cm.

A second catheter 34 may approach a second side 35 of septal defect 110 by passing through the arterial system, into the left atrium 36, and to a location within left ventricle 20 adjacent septal defect 110. Preferably, second catheter 34 comprises a proximal end located outside the patient (not shown), a distal end 38, and a second lumen 40 extending therethrough. Although named independently of first catheter 22, the features attributed to second catheter 34 and first catheter 22 are understood to be interchangeable.

A bridge member 30 may be used to couple first catheter 22 and second catheter 34. Bridge member 30 may comprise a proximal end disposed outside the patient (not shown) and a distal end 32. Bridge member 30 may be adapted to be disposed within first lumen 28 and is generally flexible. Bridge member 30 may comprise a conventional guidewire or be similar to a conventional guidewire. According to this embodiment, bridge member 30 may be about 100 to 360 centimeters long. For example, bridge member 30 may be long enough to span the length of first catheter 22, extend between first catheter 22 and second catheter 34, span the length of second catheter 22, and be accessible near the proximal ends of first catheter 22 and/or second catheter 34. Alternatively, bridge member 30 may span a portion of first catheter 22 and/or second catheter 34 and be manipulated by an actuator or activator that is coupled to bridge member 30.

Figure 3:
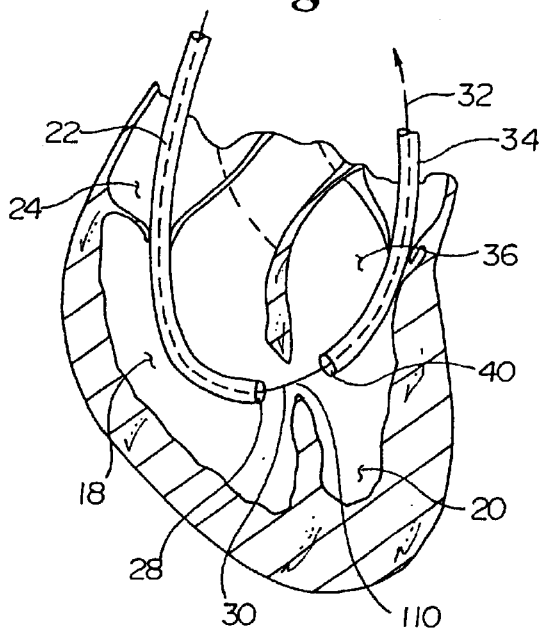
FIG. 3 is a plan view of two catheters connected by a bridge member, according to a preferred embodiment of the invention.

FIG. 3 is a plan view of two catheters connected by bridge member 30, according to a preferred embodiment of the invention. Once first catheter 22 and second catheter 30 are located on the opposite side of septal defect 110, distal end 32 of bridge member 30 may be extended so as to pass from first lumen 28, through septal defect 110, and into second lumen 40 of second catheter 34. In an exemplary embodiment, distal end 32 of bridge member 30 may continue to be extended through second lumen 40 of second catheter 34 until distal end 32 extends outside the patient proximate the proximal end of second catheter 34.

A number of techniques and features may be utilized in order to maximize the successful extension of bridge member 30 from first lumen 28 into second lumen 40. For example, any one of a number of commonly known visualization techniques (fluoroscopy, magnetic resonance imaging, etc.) may be used to visualize bridge member 30, first catheter 22, and second catheter 34 so as to assist a clinician. In addition, second lumen 40 may include a generally funnel-shaped opening that may simplify extending bridge member 30 into second lumen 40.

Figure 4:
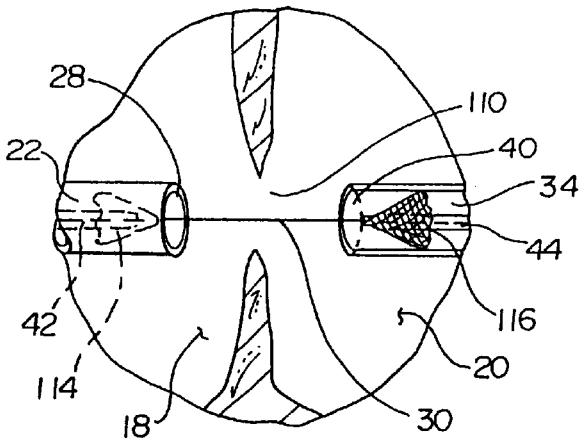
FIG. 4 is a plan view of two catheters connected by a bridge member and having two patches approaching a septal defect, according to a preferred embodiment of the invention.

FIG. 4 is a plan view of two catheters connected by bridge member 30 and having two patches approaching septal defect 110, according to a preferred embodiment of the invention. First patch 114 may be urged toward septal defect 110 along bridge member 30 from first lumen 28 of first catheter 22. A first pusher 42 may be used to urge first patch 114 along bridge member 30. First pusher 42 may comprise a catheter (e.g., a guide catheter), tool, or similar object that may come in contact with first patch 114 and may extend out of the proximal end of first catheter 22 so as to be accessible by a clinician. First pusher 42 may be adapted and configured to be disposed within first lumen 28 and be movable along bridge member 30. According to this embodiment, force applied by the clinician on first pusher 42 in the distal direction may then allow first pusher 42 to move first patch 114 over bridge member 30, toward septal defect 110.

Second patch 116 may be urged toward septal defect 110 along bridge member 30 from second lumen 40 of second catheter 34. Similar to what is disclosed above, a second pusher 44 that is essentially the same in form and function as first pusher 42 may be used to move second patch 116 over bridge member 30 toward septal defect 110. Although named independently of first patch 114, the features attributed to second patch 116 and first patch 114 are understood to be interchangeable.

The shape of first patch 114 and second patch 116 may include, but is not limited to, generally umbrella-like, concave, convex, curved, straight, and the like. For illustrative purposes, discussion regarding the shape or features of patches, according to a preferred embodiment of the invention is directed toward first patch 114, but is equally applicable to second patch 116 and other analogous elements. First patch 114 may have a diameter or width that is sized for fitting over a septal defect and a surface area suitable for covering the septal defect. First patch 114 may include a support structure coupled to a patch fabric. For example, the support structure may include a stainless steel or nickel-titanium alloy struts covered with the patch fabric. The patch fabric may be comprised of a polymeric material such as nylon, polypropylene, polytetrafluoroethylene, etc.

First patch 114 may be configured to transition between a collapsed configuration and an expanded configuration. In general, first patch 114 may be in the collapsed configuration when located within first lumen 28 of first catheter 22. The expanded configuration is understood to be generally expanded and adapted for treating septal defect 110. First patch 114 may switch to the expanded configuration when it is no longer contained within first lumen 28. According to this embodiment, first patch 114 is understood to be self-expanding. Alternatively, first patch 114 may switch to the expanded configuration when contacted or connected with second patch 116. For example, applying necessary force onto first patch 114 to couple it to second patch 116 may relieve pressure within the structure of first patch 114 that may be holding it in the collapsed configuration.

In a preferred embodiment, passing bridge member 30 from first lumen 28, through septal defect 110, and through second lumen 40 allows first patch 114 and second patch 116 to be centered across septal defect 110. According to this embodiment, first patch 114 and second patch 116 can approach opposite sides of septal defect 110 and increase the probability of properly centering across septal defect 110.

Figure 5:
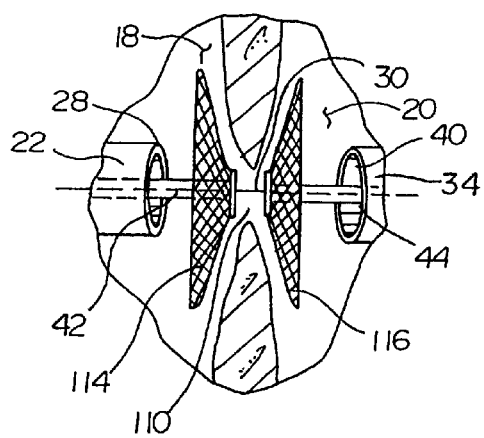
FIG. 5 is a plan view of two catheters connected by a bridge member and having two patches sealing a septal defect, according to a preferred embodiment of the invention.

FIG. 5 is an enlarged view of two catheters connected by bridge member 30 and having two patches sealing septal defect 110, according to a preferred embodiment of the invention. According to a preferred embodiment, first patch 114 may be urged toward septal defect 110 along bridge member 30 by first pusher 42, and second patch 116 may be urged toward septal defect 110 along bridge member 30 by second pusher 44. FIG. 5 depicts both first patch 114 and second patch 116 in expanded configurations. However, in alternative embodiments of the invention, first patch 114 and second patch 116 may not be in the expanded configuration until they connect to one another.

Figure 6:
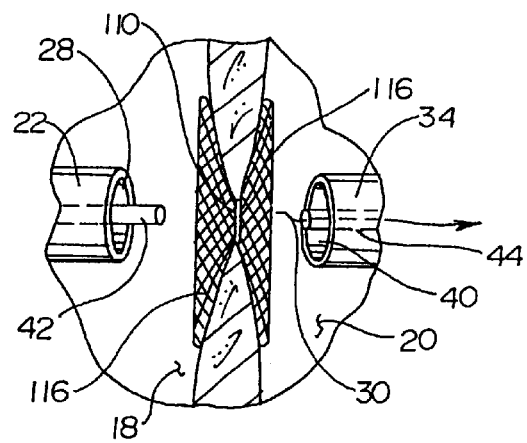
FIG. 6 is a plan view of two catheters withdrawing from a repaired septal defect, according to a preferred embodiment of the invention.

FIG. 6 is an enlarged view of two catheters withdrawing from a repaired septal defect, according to a preferred embodiment of the invention. First patch 114 and second patch 116 are connected across septal defect 110. After first patch 114 and second patch 116 have been disposed at septal defect 110, first catheter 22, first pusher 42, second catheter 34, second pusher 44, and bridge member 30 may be removed from the patient by withdrawing the catheters through the vasculature.

As suggested by FIG. 6, connecting first patch 114 and second patch 116 need not necessarily constitute a perfect seal across septal defect 110, since the removal of bridge member 30 will likely leave a small opening within first patch 114 and second patch 116. Rather, it is the patching of a substantial portion of septal defect 110 that is necessary to treat a septal defect. This is because substantially sealing the defect can result in generation of thrombus that can complete the seal.

In alternative embodiments of the invention, first patch 114 and second patch 116 may be connected by differing mechanisms. Examples of these mechanisms are depicted in FIGS. 7–11. In the following description, features attributed to various embodiments of a first patch and a second patch are interchangeable.

Figure 7:
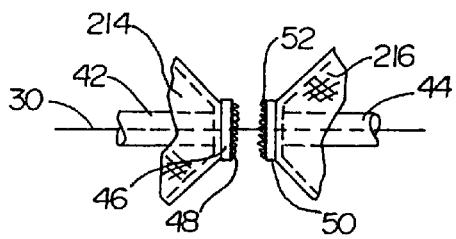
FIG. 7 is a detailed view of hook and loop connectable patch devices, according to a preferred embodiment of the invention.

FIG. 7 is a detailed view of hook and loop connectable patch devices, according to a preferred embodiment of the invention. According to this embodiment, first patch 214 comprises an outer surface 46 having a plurality of loops 48. In addition, second patch 216 comprises an outer surface 50 having a plurality of hooks 52 that are complementary to loops 48. Hooks 52 may engage loops 48 when first patch 214 and second patch 216 are brought into contact with one another. Preferably, hooks 52 and loops 48 may engage sufficiently so that first patch 214 and second patch 216 substantially remain connected.

Figure 8:
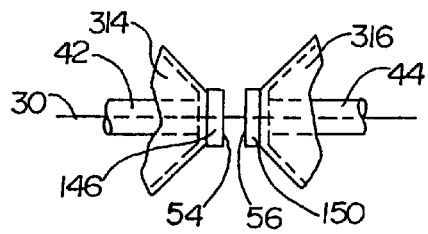
FIG. 8 is a detailed view of magnet connectable patch devices, according to a preferred embodiment of the invention.

FIG. 8 is a detailed view of magnet connectable patch devices, according to a preferred embodiment of the invention. According to this embodiment, first patch 314 comprises outer surface 146 including a magnet 54. In addition, second patch 316 comprises outer surface 150 including a magnet 56 that has a polarity that is opposite to magnet 54. Magnet 54 may engage magnet 56 when first patch 314 and second patch 316 are brought into contact with one another. Preferably, magnet 54 and magnet 56 may engage sufficiently so that first patch 314 and second patch 316 substantially remain connected.

Figure 9:
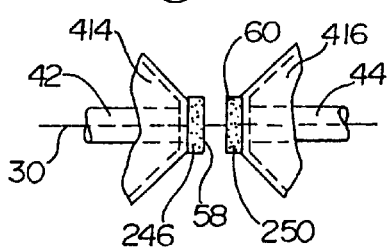
FIG. 9 is a detailed view of adhesive connectable patch devices, according to a preferred embodiment of the invention.

FIG. 9 is a detailed view of adhesive connectable patch devices, according to a preferred embodiment of the invention. According to this embodiment, first patch 414 comprises outer surface 246 including adhesive 58. In addition, second patch 416 comprises outer surface 250 including adhesive 60. Adhesive 58 may engage adhesive 60 when first patch 414 and second patch 416 are brought into contact with one another and couple first patch 414 to second patch 416. For example, adhesive 58 and adhesive 60 may be chemically compatible such that direct contact of the adhesives causes a chemical reaction between the adhesives that couples first patch 414 to second patch 416. Alternatively, adhesive 58 and/or adhesive 60 may be contained within a reservoir that may release upon one of the adhesives upon contact between the patches. For example, first patch 414 may include a penetrating member adapted to penetrate and release the adhesive from the reservoir. Moreover, adhesive 58 and/or adhesive 60 may be covered by a removable covering that, upon moving the covering, would make available the adhesive.

In a preferred embodiment, adhesive 58 or adhesive 60 may comprise fibrinogen, fibrin, fibrinase, plasmin, fibrinolysin, cyanoacrylate, menadiol sodium diphosphate, phytomenadione, thrombin, and combinations thereof. In general, adhesive 58 may comprise any substance capable of holding first patch 414 and second patch 416 together that is substantially biocompatible.

Figure 10:
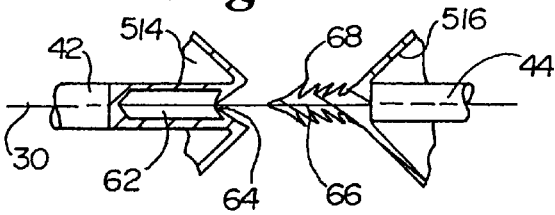
FIG. 10 is a detailed view of mechanically connectable patch devices, according to a preferred embodiment of the invention.

FIG. 10 is a detailed view of mechanically connectable patch devices, according to a preferred embodiment of the invention. According to this embodiment, first patch 514 comprises a chamber 62 and a deflectable flange 64. In addition, second patch 516 comprises a shank 66 having one or more rings defining recesses 68 therebetween. Preferably, chamber 62 is adapted to receive shank 66 and lock in place when deflectable flange 64 becomes disposed within a recess 68. When first patch 514 and second patch 516 are locked, they remain connected.

Figure 11:
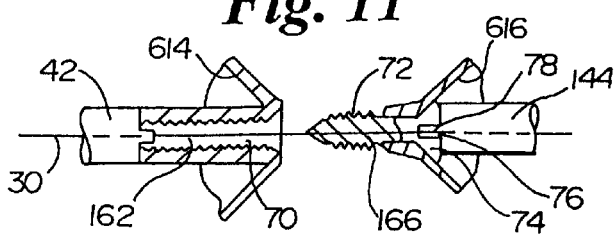
FIG. 11 is a detailed view of alternative mechanically connectable patch devices, according to a preferred embodiment of the invention.

FIG. 11 is a detailed view of an alternative mechanically connectable patch device, according to a preferred embodiment of the invention. According to this embodiment, first patch 614 comprises chamber 162 having threads 70. Preferably, these features of first patch 614 are analogous to that of a threaded nut. In addition, second patch 616 comprises shank 166 having a thread 72. Second patch 616 further comprises a head 74 having a slot 76. Preferably, these features of second patch 616 are analogous to that of a bolt or screw. An alternative pusher, for example, second pusher 144, may be used that includes a complementary head 78 adapted to engage slot 76. According to this embodiment, second pusher 144 and second patch 616 have mating ends and second pusher 144 may comprise features analogous to a flexible screwdriver. Preferably, chamber 162 is adapted to threadably receive shank 166. Rotation of second pusher 144 while complementary head 78 is engaged with slot 76 may allow second patch 616 to threadably engage chamber 162 in a manner analogous to using a screwdriver to thread a nut and bolt. When first patch 614 and second patch 616 are threaded, they remain connected.

Numerous advantages of the invention covered by this document have been set forth in the foregoing description. It will be understood, however, that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A system for treating septal defects, comprising:
   a first catheter having a distal end and a first lumen;
   a second catheter having a distal end and a second lumen;
   a bridge member extending between the distal end of the first catheter and the distal end of the second catheter, wherein the bridge member is disposed within both the first lumen and the second lumen; and
   a first patch adapted to be disposed within the first lumen and movable out of the first lumen along the bridge member.

2. The system in accordance with claim 1, wherein the distal end of the first catheter and the distal end of the second catheter face each other.

3. The system in accordance with claim 1, further comprising a second patch adapted to be disposed within the second lumen and movable out of the second lumen along the bridge member.

4. The system in accordance with claim 3, wherein the first patch and the second patch are connectable.

5. The system in accordance with claim 1, wherein the first patch further comprises a hook.

6. The system in accordance with claim 5, wherein the second patch includes a loop.

7. The system in accordance with claim 1, wherein the first patch includes an adhesive.

8. The system in accordance with claim 7, wherein the adhesive includes fibrigen.

9. The system in accordance with claim 7, wherein the adhesive includes fibrin glue.

10. The system in accordance with claim 7, wherein the adhesive includes cyanoacrylate.

11. The system in accordance with claim 1, wherein the first patch further comprises a shank.

12. The system in accordance with claim 11, wherein the first patch further comprises threads.

13. The system in accordance with claim 11, wherein the first patch further comprises one or more rings disposed on the shank defining a recess therebetween.

14. The system in accordance with claim 13, wherein the second patch further comprises a deflectable flange.

15. The system in accordance with claim 1, further comprising a first pusher to urge the first patch out of the first lumen along the bridge member.

16. The system in accordance with claim 15, wherein the first patch and the first pusher have mating ends.

17. A method for treating septal defects, comprising the steps of:
   providing a first catheter including a first lumen;
   advancing the first catheter through the vasculature of a patient to a first side of a septal defect;
   providing a second catheter including a second lumen;
   advancing the second catheter through the vasculature of a patient to a second side of the septal defect;
   passing a bridge member from the first lumen into the second lumen, the bridge member spanning between the first catheter and the second catheter and passing through the septal defect; and
   passing a first patch from the first lumen over the bridge member to the first side of the septal defect.

18. The method in accordance with claim 17, wherein the step of advancing the first catheter through the vasculature of a patient to a first side of a septal defect includes passing the first catheter through an atrium.

19. The method in accordance with claim 17, wherein the step of advancing the second catheter through the vasculature of a patient to a second side of a septal defect includes passing the second catheter through an atrium.

20. The method in accordance with claim 17, wherein the first catheter is located on the first side of the septal defect in an atrium.

21. The method in accordance with claim 17, wherein the first catheter is located on the first side of the septal defect in a ventricle.

22. The method in accordance with claim 17, further comprising the step of passing a second patch from the second lumen over the bridge member to the second side of the septal defect.

23. The method in accordance with claim 22, further comprising the step of connecting the first patch and the second patch.

24. A method for treating septal defects, comprising the steps of:
   providing a first catheter including a first lumen;
   advancing the first catheter through the vasculature of a patient to a first side of a septal defect;
   providing a second catheter including a second lumen;
   advancing the second catheter through the vasculature of a patient to a second side of the septal defect;
   passing a bridge member from the first lumen into the second lumen, the bridge member spanning between the first catheter and the second catheter and passing through the septal defect;
   urging a first patch from the first lumen over the bridge member to the first side of the septal defect with a first pusher;
   urging a second patch from the second lumen over the bridge member to a second side of the septal defect with a second pusher; and
   connecting the first patch and the second patch across the septal defect.

25. The method in accordance with claim 24, wherein the step of advancing the first catheter through the vasculature of a patient to a first side of a septal defect includes passing the first catheter through an atrium.

26. The method in accordance with claim 24, wherein the step of advancing the second catheter through the vasculature of a patient to a second side of a septal defect includes passing the second catheter through an atrium.

27. The method in accordance with claim 24, wherein the first catheter is located on the first side of the septal defect in an atrium.

28. The method in accordance with claim 24, wherein the first catheter is located on the first side of the septal defect in a ventricle.

* * * * *